United States Patent [19]

Ueno et al.

[11] Patent Number: 5,126,372
[45] Date of Patent: Jun. 30, 1992

[54] EXCRETION OF NONPROTEIN NITROGEN INTO THE INTESTINE BY PROSTANOIC ACID DERIVATIVES

[75] Inventors: Ryuji Ueno; Hiroyoshi Osama, both of Hyogo, Japan

[73] Assignee: K.K. Ueno Seiyaku Oyo Kenkyujo, Osaka, Japan

[21] Appl. No.: 564,489

[22] Filed: Aug. 8, 1990

[30] Foreign Application Priority Data

Aug. 9, 1989 [JP] Japan .................................. 1-205895

[51] Int. Cl.$^5$ ..................... A61K 31/19; A61K 31/215
[52] U.S. Cl. ..................................... 514/530; 514/573
[58] Field of Search ................................. 514/573, 530

[56] References Cited

FOREIGN PATENT DOCUMENTS

| | | |
|---|---|---|
| 0281239 | 1/1988 | European Pat. Off. . |
| 0284180 | 1/1988 | European Pat. Off. . |
| 0330511 | 2/1988 | European Pat. Off. . |
| 0289349 | 4/1988 | European Pat. Off. . |
| 0292177 | 5/1988 | European Pat. Off. . |
| 0308135 | 9/1988 | European Pat. Off. . |
| 0310305 | 9/1988 | European Pat. Off. . |
| 0342003 | 5/1989 | European Pat. Off. . |
| 0343904 | 5/1989 | European Pat. Off. . |
| 0345951 | 5/1989 | European Pat. Off. . |

OTHER PUBLICATIONS

Anggard, Acta physiol. scand, 1966, 66, pp. 509–510.
Robert, et al., Prostaglandins, vol. 11, No. 5, May 1976, pp. 809–828.
Roman, et al. "Prostaglandin $E_2$ and $F_{2a}$ reduces urea reabsorption . . . duct", Am. J. Physiol., 1981, 241(1), F53–F60.
Zook, Diss Abstr. Int, B 1980, 41(3) pp. 918–919.
Nagamatsu, et al., Inflammation, vol. 2, No. 4, (1982), pp. 317–318 and Translation.
Chem. Abst. 93 (1980) pp. 180, 121 S.
Chem. Abst. 95 (1981), p. 74304k.

*Primary Examiner*—S. J. Friedman
*Attorney, Agent, or Firm*—Sughrue, Mion, Zinn, Macpeak & Seas

[57] ABSTRACT

A method for improvement of excretion of nonprotein nitrogen into the intestines which comprises administering, to a subject in need of such improvement, a prostanoic acid derivative in an amount effective in improving excretion of nonprotein nitrogen into the intestines.

16 Claims, No Drawings

EXCRETION OF NONPROTEIN NITROGEN INTO THE INTESTINE BY PROSTANOIC ACID DERIVATIVES

BACKGROUND OF THE INVENTION

1. Field of the Invention

The present invention relates to a method for improvement of excretion of nonprotein nitrogen into the intestines which comprises administering a prostanoic acid derivative to a subject.

The object of the present invention is to improve excretion, via the intestinal wall, of nonprotein nitrogen such as urea nitrogen, creatinine etc., as the substitute means for the treatment, such as extracorporeal dialysis, peritoneal dialysis, etc., for removal of the above nitrogens, in a subject whose nonprotein nitrogen concentration in the blood is elevated by e.g. renal insufficiency.

Renal insufficiency refers to a condition in which renal function is injured by renal diseases such as glamerulonephritis, nephrotic syndrome, nephrosclerosis, renal carcinoma, lupus nephritis etc. One important parameter for renal insufficiency is the excreting function of kidney an especially the concentration of nonprotein nitrogen such as urea, creatinine etc. in the blood which are pooled in the body by injured excretion. Symptom of uremia appears as the pooling progresses.

Traditional means effective in the treatment of renal insufficiency is the so-called dialysis in which the blood is contacted with a dialysate with a semipermeable membrane between them whereby substances in the blood may be removed through diffusion by osmotic gradient. The dialysis include hemokialysis in which the arterial blood is introduced into an artificial kidney and returned to a vein and peritoneal dialysis in which blood substances are dispersed into a dialysate, which is introduced into the peritoneal cavity and discharged periodically, through capillary vessels serving as a semipermeable membrane. However, the former has disadvantage that it requires a sergical operation such as shunt operation while the latter has disadvantages that it has inferior dialysis efficacy and requires infection-preventing measures.

BACKGROUND INFORMATION

The present inventor and co-workers formerly discovered that 15-keto-16-halo-prostaglandins (hereinafter, prostaglandin is referred to as PG) have an enteropooling activity (activity of pooling water in intestines) (EP-A-310305). Enteropooling activity of 16,16-dimethyl-PGE$_2$ has also been described in Prostaglandins, 11, 809–828(1976). However, nothing has been reported about a compound having an activity of excreting nonprotein nitrogen into intestines.

As a result of extensive studies about the properties of PG compounds, the present inventors unexpectedly discovered that these compounds have an activity of excreting nonprotein nitrogen in the blood into the intestines.

SUMMARY OF THE INVENTION

In a first aspect, the present invention provides a method for improvement of excretion of nonprotein nitrogen into the intestines which comprises administering, to a subject in need of such improvement, a prostanoic acid derivative in an amount effective in improving excretion of nonprotein nitrogen into the intestines.

In a second aspect, the present invention provides a use of a prostanoic acid derivative for the manufacture of a medicament for improvement of excretion of nonprotein nitrogen into the intestine.

In a third aspect, the present invention provides a pharmaceutical composition for improvement of excretion of nonprotein nitrogen into the intestine comprising a prostanoic acid derivative in association with a pharmaceutically acceptable carrier, diluent or excipient.

DETAILED DESCRIPTION OF THE INVENTION

As used herein, the term "nonprotein nitrogen" includes urea, uric acid, creatine, creatinine, amino acids, ammonia etc., with urea and creatinine being most important.

The words "excretion into the intestine" mean active or passive transport of substances (water, nonprotein nitrogen etc.) in the body fluid, principally in the blood, into the intestine ranging from duodenum to large intestine, principally into small intestine.

The term "prostanoic acid" refers to the basic skeleton, shown by the formula below, as the common structural feature of the naturally occurring PGs.

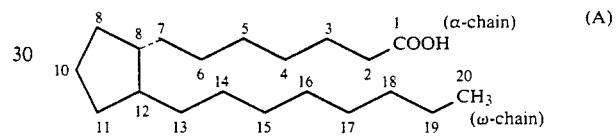

The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

Subscript 1—15-OH
Subscript 2—5,6-unsaturated-15-OH
Subscript 3—5,6- and 17, 18-diunsaturated-15-0H Further, PGFs are sub-classified according to the configuration of hydroxy group at 9 into α(hydroxy group being in the alpha configuration) and β(hydroxy group being in the beta configuration). Some synthetic analogues have somewhat modified skeletons.

The term "derivative" refers to a compound in which one or more atom or group in the prostanoic acid shown by the formula (A) is replaced by other atom or group or eliminated. Such derivatization includes the modifications known in the synthetic PG analogues and other modifications.

Nomenclature

Nomenclature of prostanoic acid derivatives herein uses the numbering system of prostanoic acid represented in formula (A) shown above.

While formula (A) shows a basic skeleton having twenty carbon atoms, the 15-keto-PG compounds used in the present invention are not limited to those having the same number of carbon atoms The carbon atoms in Formula (A) are numbered 2 to 7 on the a-chain starting from the a-carbon atom adjacent to the carboxylic carbon atom which is numbered 1 and towards the five-membered ring, 8 to 12 on the said ring starting from the carbon atom on which the a-chain is attached, and 13 to 20 on the s-chain starting from the carbon atom adjacent to the ring. When the number of carbon atoms is decreased in the a-chain, the number is deleted in order starting from position 2 and when the number of carbon atoms is increased in the a-chain, compounds are named as substituted derivatives having respective substituents at position 1 in place of carboxy group (C-1). Similarly, when the number of carbon atoms is decreased in the s-chain, the number is deleted in order starting from position 20 and when the number of carbon atoms is increased in the s-chain, compounds are named as substituted derivatives having respective substituents at position 20. Stereochemistry of the compounds is the same as that of above formula (A) unless otherwise specified.

In general, PGDs, PGEs and PGFs have (a) hydroxy group(s) on the carbon atom(s) at position 9 and/or 11 but in the present specification PGs include those having a group other than a hydroxyl group at position 9 and/or 11. Such PGs are referred to as 9-dehydroxy-9-substituted-PG compounds or 11-dehydroxy-11-substituted-PG compounds.

As stated above, nomenclature of the prostanoic acid derivative is based upon the prostanoic acid and sometimes utilizes abbreviation "PG" for convenience, when the derivative in question has a partial structural common with PGs. These compounds, however, can also be named according to the IUPAC naming system. For example, 13,14-dihydro-15-keto-16R,S-fluoro-PGE$_2$ is (Z)-7-{(1R,2R,3R)-3-hydroxy-2-[(4R,S)-4-fluoro-3-oxo-1-octyl]-5-oxocyclopentyl}-hept-5- enic acid. 13,14-dihydro-15-keto-20-ethyl-11-dehydroxy-11R-methyl-PGE$_2$ methyl ester is methyl 7-{(1R,2S,3S)-3-methyl-2-[3-oxo-1-decyl]-5-oxo-cyclopentyl}-hept-5-enoate. 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxo-cyclopentyl}-6-oxo-heptanoate. 13,14-dihydro-15-keto- 20-ethyl-PGF$_{2\alpha}$ isopropyl ester is isopropyl (Z)-7-[(1R,2R,3R,5S)-3,5-dihydroxy-2-{3-oxo-1-decyl)-cyclopentyl]-hept-5-enoate. 13,14-dihydro-15-keto-20-methyl-PGF$_{2\alpha}$ methyl ester is methyl (Z)-7-[(1R,2R,3R,5S)-3,5-dihydroxy-2-{3-oxo-1-nonyl}-cyclopentyl]-hept-5-enonate.

Preferred Compounds

Preferred prostanoic acid derivatives used in the present are those having an oxo group at position 15 of the prostanoic acid in place of the hydroxy group, or having at least one halogen atom on the prostanoic acid skeleton, or having both of these features These derivatives may have a single bond (15-keto-PG$_1$ compounds), a double bond (15-keto-PG$_2$ compounds) between positions 5 and 6, or two double bonds (15-keto-PG$_3$ compounds) between positions 5 and 6 as well as positions 17 and 18.

The term "halogen" refers to fluorine, chlorine, bromine and iodine with fluorine being preferred.

Examples of substitution products or derivatives include esters at the carboxy group at the alpha chain, pharmaceutically or physiologically acceptable salts, unsaturated derivatives having a double bond or a triple bond between positions 2 and 3 or positions 5 and 6, respectively, substituted derivatives having substituent(s) on carbon atom(s) at position 3, 6, 16, 17, 19 and/or 20 and compounds having lower alkyl or a hydroxy (lower) alkyl group at position 9 and/or 11 in place of the hydroxy group, of the above PGs.

Examples of substituents present in preferred compounds are as follows: Substituents on the carbon atom at position 3, 17 and/or 19 include lower alkyl, for example, C$_{1-4}$ alkyl, especially methyl and ethyl. Substituents on the carbon atom at position 16 include lower alkyl e.g. methyl, ethyl etc., hydroxy and halogen atom e.g. chlorine, fluorine, phenyl and phenoxy, the last two being unsubstituted or substituted. Substituents on the carbon atom at position 20 include saturated and unsaturated lower alkyl e.g. C$_{1-4}$ alkyl, lower alkoxy e.g. C$_{1-4}$ alkoxy and lower alkoxy (lower) alkyl e.g. C$_{1-4}$ alkoxy-C$_{1-4}$ alkyl. Substituents on the carbon atom at position 6 include oxo group forming carboxyl. Stereochemistry of PGs having hydroxy, lower alkyl or lower (hydroxy) alkyl substituent on the carbon atom at position 9 and/or 11 may be alpha, beta or mixtures thereof.

Said derivatives may have an alkoxy, phenoxy or phenyl group at the end of the omega chain where the chain is shorter than the primary PGs.

In the present invention, preferred compounds are those having at least one halogen atom on the prostanoic acid derivative, and the position of halogen atom is not limited but preferredly on the omega chain and more preferredly one or two halogen atoms are present at position 16.

A group of preferred compounds used in the present invention has the formula (I)

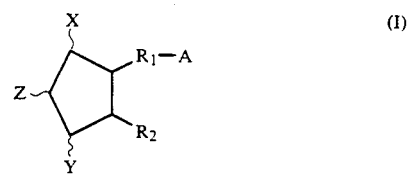

wherein X and Y are hydrogen, hydroxy, halo, lower alkyl, hydroxy(lower)alkyl, or oxo, with the proviso that at least one of X and Y is a group other than hydrogen, and 5-members ring may have at least one double bond, Z is hydrogen or halogen, A is —CH$_2$OH, —COCH$_2$OH, —COOH or its functional derivative, R$_1$ is bivalent saturated or unsaturated, lower or medium aliphatic hydrocarbon residue which is unsubstituted or substituted with halo, oxo or aryl, R$_2$ is saturated or unsaturated, lower or medium aliphatic hydrocarbon residue which is unsubstituted or substituted with oxo, hydroxy, halo, lower alkoxy, lower alkanoyloxy, cyclo(lower)alkyl, aryl or aryloxy, with the proviso the third carbon atom counted from 5-membered ring is substituted with an oxo group.

In the above formula, the term "unsaturated" in the definitions for R$_1$ and R$_2$ is intended to include at least one and optionally more then one double bond and/or triple bond isolatedly, separately or serially present between carbon atoms of the main and/or side chains According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarbyl group having 1 to 14 carbon atoms (for a side chain, 1 to 3 carbon atoms being preferred) and preferably 2 to 8 carbon atoms for R$_1$ and 6 to 12 carbon atoms for R$_2$.

The term "halo" denotes fluoro, chloro, bromo and iodo.

The term "lower" is intended to include a group having 1 to 6 carbon atoms unless otherwise specified.

The term "lower alkyl" as a group or a moiety in hydroxy(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkoxy" refers to the group lower-alkyl-O- wherein lower alkyl is as defined above.

The term "hydroxy(lower)alkyl" refers to alkyl as defined above and substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower)alkyl wherein halo and lower alkyl being as defined above.

The term "aryloxy" refers to a group of the formula: ArO- wherein Ar is aryl as defined above.

The term "functional derivative" of carboxy as A includes salts (preferably pharmaceutically acceptable salts), esters and amides.

Suitable "pharmaceutically acceptable salts" includes conventional non-toxic salts, and may be a salt with an inorganic base, for example a metal salt such as an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)methane salt, monomethylmonoethanolamine salt, procaine salt, caffeine salt, etc.), a basic amino acid salt (e.g. arginine salt, lysine salt, etc.), tetraalkylammonium salt and the like. These salts can be prepared by the conventional process, for example from the corresponding acid and base or by salt interchange.

Examples of the esters are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower) alkyl ester e.g. hydroxyethyl ester, lower alkoxy(lower)-alkyl ester e.g. methoxymethyl ester, 1-methoxyetyl ester, etc., and aromatic esters, for example, optionally substituted aryl ester e.g. phenyl ester, tosyl ester, t-butylphenyl ester, salicyl ester, 3,4-di-methoxyphenyl ester, benzamidophenyl ester etc., aryl(lower)alkyl ester e.g. benzyl ester, trityl ester, benzhydryl ester, etc. Examples of the amides are mono- or di- lower alkyl amides e.g. methylamide, ethylamide, dimethylamide, etc., arylamide e.g. anilide, toluidide, and lower alkyl- or aryl-sulfonylamide e.g. methylsulfonylamide, ethylsulfonylamide, tolylsulfonylamide etc.

Preferred examples of A include —COOH, —COOCH$_3$, —COOCH$_2$CH$_3$, COOCH(CH$_3$)$_2$ and —CONHSO$_2$CH$_3$.

The configuration of the ring and the α- and/or omega chain in the above formula (I) may be the same as or different from that in the primary PGs. However, the present invention also includes a mixture of a compound having a primary configuration and that of an unprimary configuration.

Examples of the typical compounds of the present invention are 15-keto-PGs, 13,14-dihydro-15-keto-PGs and their e.g. 6-keto-derivatives, Δ$^2$-derivatives, 3R,S-methyl-derivatives, 16R,S-methylderivatives, 16,16-dimethyl-derivatives, 16R,S-fluoroderivatives, 16,16-difluoro-derivatives, 17S-methylderivatives, 19-methyl-derivatives, 20-methyl-derivatives and 16-desbutyl-16-phenoxy derivatives.

When 15-keto-PG compounds of the present invention have a saturated bond between positions 13 and 14, these compounds may be in the keto-hemiacetal equilibrium by forming a hemiacetal between hydroxy group at position 11 and ketone at position 15.

The proportion of both tautomeric isomer, when present, varies depending on the structure of the rest of the molecule or kind of any substituent present and, sometimes, one isomer may predominantly be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publication (unexamined) No. A-52753/1989.

Alternatively, these compounds may be prepared by a process analogous to that described herein or to known processes.

A practical preparation of the prostanoic acid derivative, e.g. 13,14-dihydro-15-keto compounds, involves the following steps; referring to the synthetic charts(I) to (III), reaction of the aldehyde (2) prepared by the Collins oxidation of commercially available (—)-Corey lactone (1) with dimethyl (2-oxoheptyl)phosphate anion to give α,β-unsaturated ketone (3), reduction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs wherein the ω-chain is a 13,14-dihydro-15-keto-alkyl group is prepared.

Using the above tetrahydropyranyl ether (7), 6-keto-PGE$_1$s (15) of which a group constituted with carbon atoms of position 5, 6 and 7 is $$-CH_2-C(O)-CH_2-,$$
$$\phantom{-}5\phantom{CH_2-}6\phantom{C(O)-}7\phantom{CH_2-}$$

may be prepared in the following steps; reduction of the tetrahydropyranyl ether (7) with, for example, diisobutyl aluminum hydride to give the corresponding lactol (8), reaction of the lactol (8), with the glide generated from (4-carboxybutyl)triphenyl phosphonium bromide followed by esterification (10), cyclization between the 5,6-double bond and the hydroxyl group at position 9 with NBS or iodine to give the halogenated compound (11), dehydrohalogenation of the compound (11) with, for example, DBU to give the 6-keto compound (13) followed by Jones oxidation and removal of the protecting groups.

Furthermore, PGE$_2$s (19) of which a group constituted with carbon atoms of position 5, 6 and 7 is $$-CH_2-CH=CH-$$
$$\phantom{-}7\phantom{CH_2-}6\phantom{CH=}5\phantom{CH-}$$

may be prepared in the following steps; as shown in the synthetic chart II, reduction of the above tetrahydropyranyl ether (7) to give the lactol (8), reaction of the resultant lactol (8) with the glide derived from (4-carboxybutyl-)triphenyl phosphonium bromide to give the carboxylic acid (16) followed by esterification to give ester (17), Jones oxidation of the esters (17) to give the compound (18), and removal of the protecting groups.

Using the above tetrahydropyranyl ether (7) as the starting material, the compound having $$-CH_2-CH_2-CH_2-$$
$$\phantom{-}7\phantom{CH_2-}6\phantom{CH_2-}5\phantom{CH_2-}$$

may be prepared by using the same process as that for preparing PGE$_2$ having $-CH_2CH=CH-$ and subjecting the resultant compound (18) to catalytic reduction to reduce the double bond between the position 5 and 6 followed by removal of the protective groups.

Synthesis of 5,6-dehydro-PGE$_2$s having $$-CH_2-C\equiv C-$$
$$\phantom{-}7\phantom{CH_2-}6\phantom{C\equiv}5\phantom{C-}$$

may be carried out by capturing a copper enolate formed by 1,4-addition of a monoalkylcopper complex or a dialkylcopper complex of the following formulae:

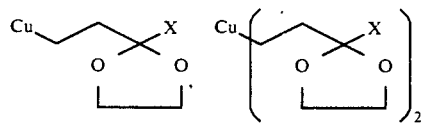

to 4R-t-butyldimethylsilyloxy-2-cyclopenten-1-one with 6-alkoxycarbonyl-1-iodo-2-hexyne or the derivatives.

The 11-$\beta$ type PGEs can be prepared according to the synthetic chart III.

PGE derivatives having a methyl group at position 11 in place of hydroxy can be prepared by reacting a dimethyl copper complex with PGA-type compound obtained by subjecting 9-hydroxy-11-tosylate to the Jones oxidation. Alternatively, they can be prepared by protecting the carbonyl of saturated ketone (4) produced by reducing unsaturated ketone (3), eliminating p-phenylbenzoyl and tosylating the produced alcohol, treating with DBU to form a lactol, introducing the alpha-chain by Wittig reaction, oxidizing the alcohol at position 9 to give PGA-type compound, and reacting the product with dimethyl copper complex in order to introduce a methyl group into position 11 to give an 11-methyl-PGE-type compound, which on reduction with e.g. sodium borohydride gives an 11-methyl-PGF-type compound. An 11-hydroxymethyl-PGE-type compound, is obtained by a benzophenone-sensitized photoaddition of methanol of PGA-type compound, which is reduced with, e.g. sodium borohydride, to give an 11-hydroxymethyl-PGF-type compound. The synthetic route for the compounds used in the present invention is not limited to the that described above one and may vary using different protecting, reducing and/or oxidizating methods.

Corresponding other PG compounds can be produced analogously.

Synthetic Chart I

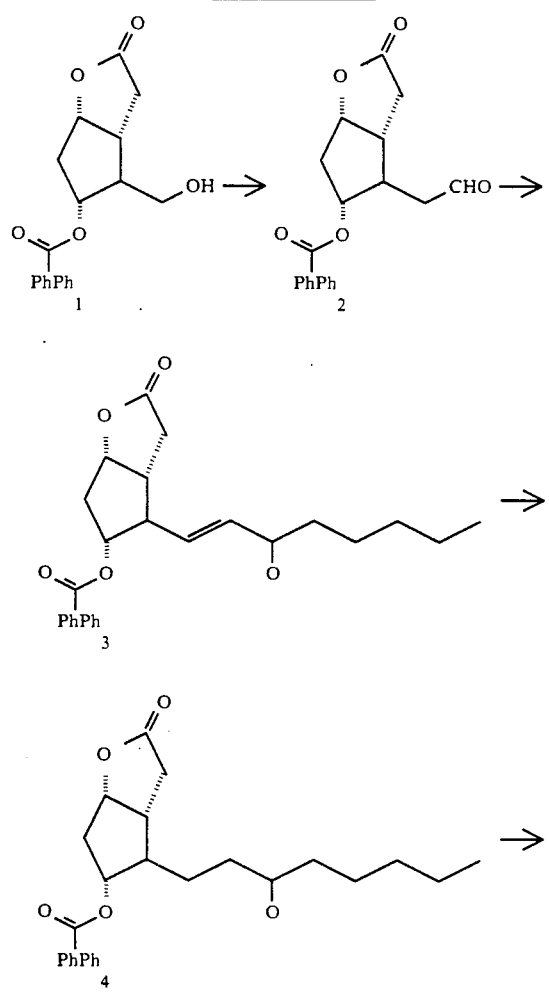

-continued
Synthetic Chart I
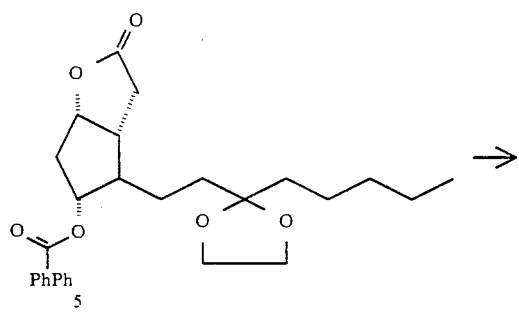
5
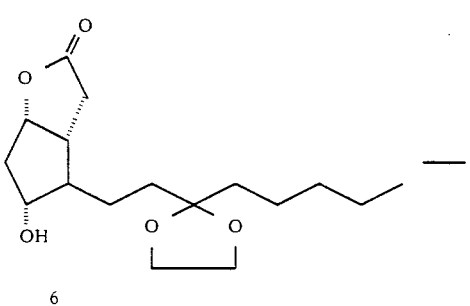
6
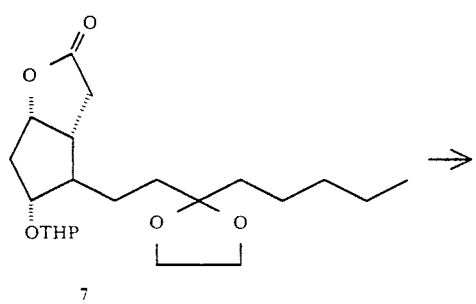
7
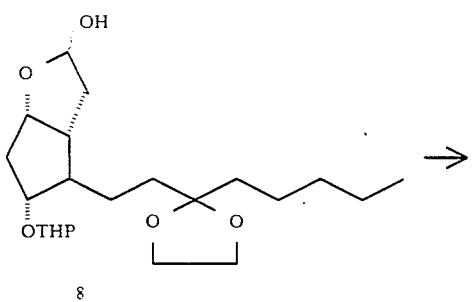
8
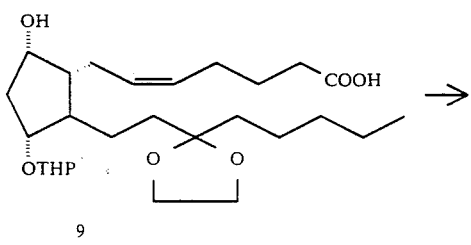
9
-continued
Synthetic Chart I
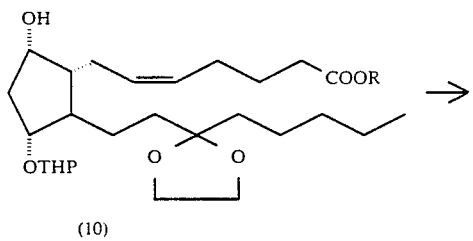
(10)
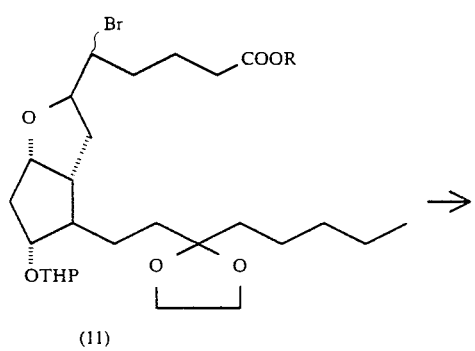
(11)
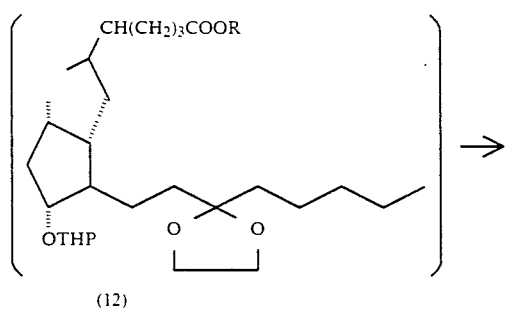
(12)
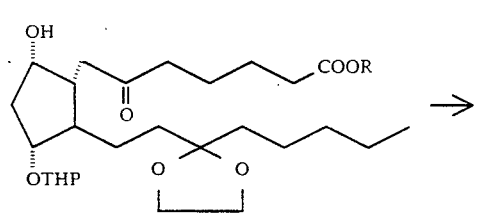
(13)
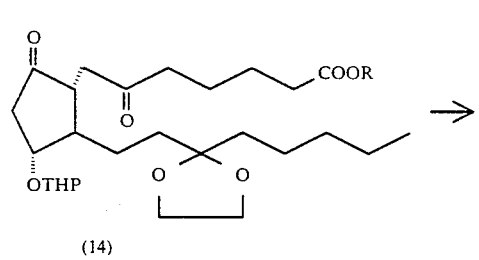
(14)
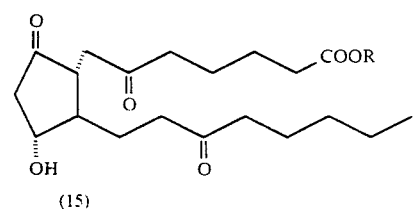
(15)

-continued
Synthetic Chart I
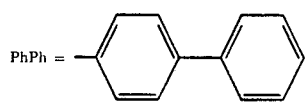
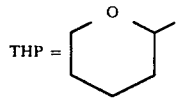
Synthetic Chart II
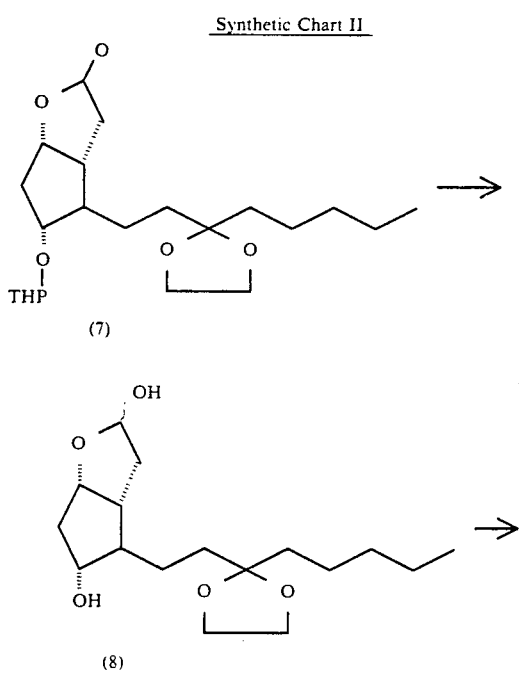
-continued
Synthetic Chart II
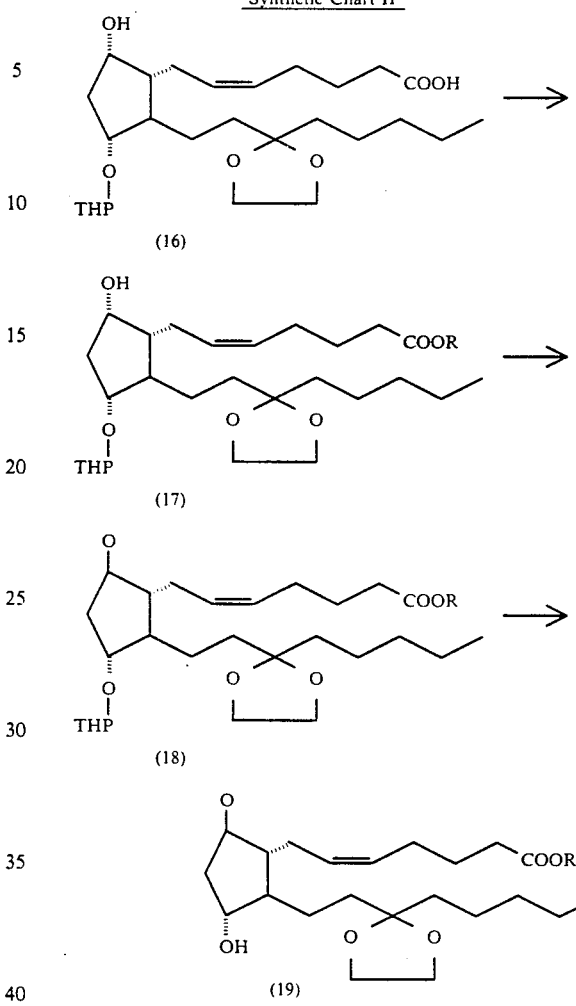
Synthetic Chart III
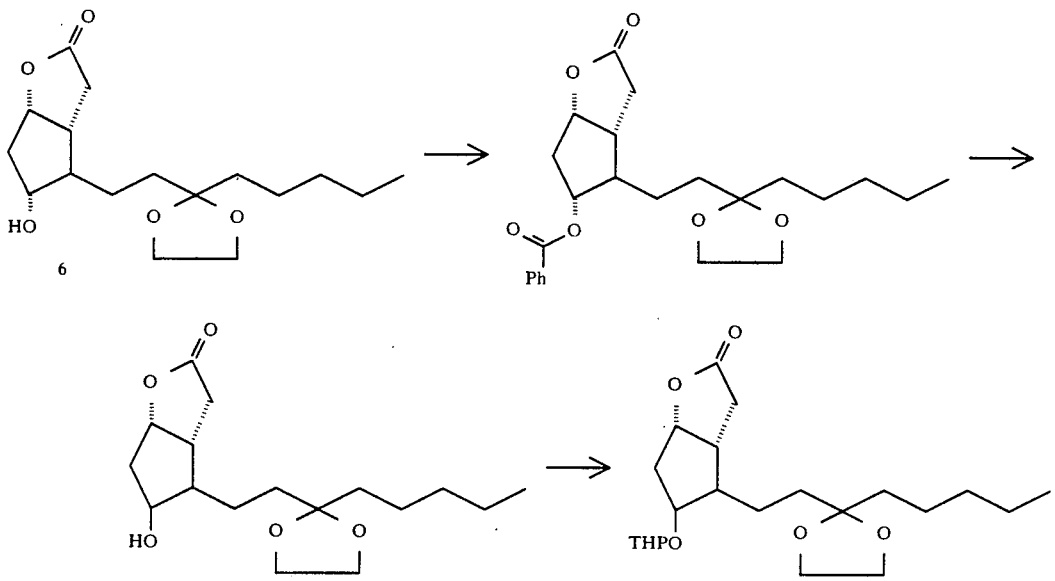

-continued
Synthetic Chart III

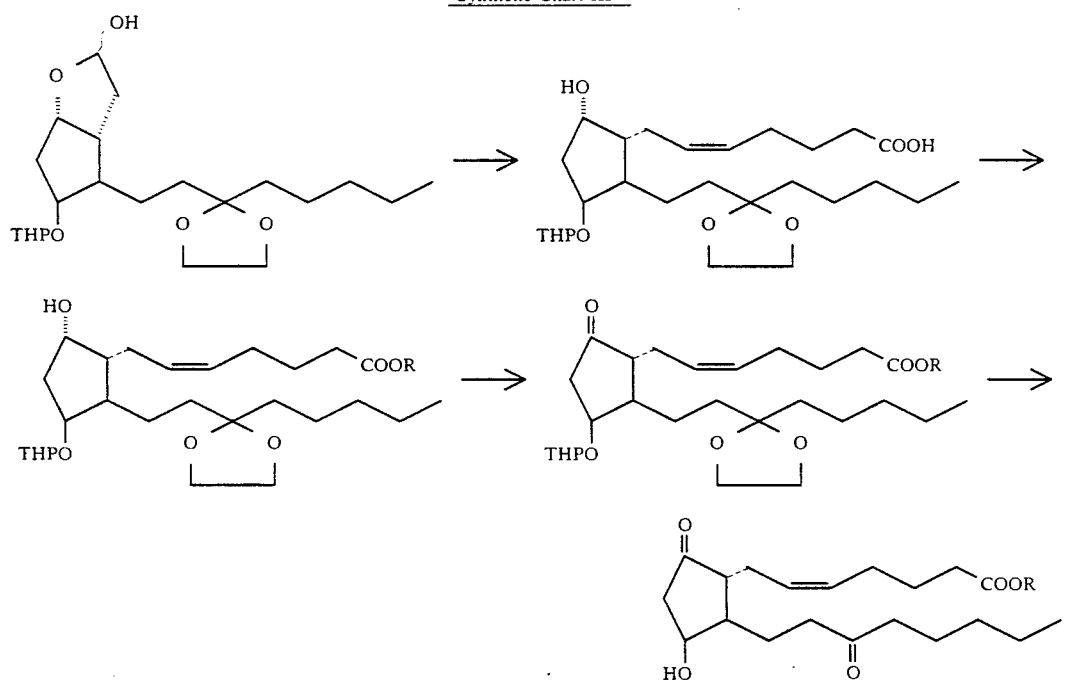

The compounds used in the present invention may be used as a medicine for animals and human beings and usually applied systemically or locally by such methods as oral administration, intravenous injection (including instillation), subcutaneous injection, suppository and the like. While the dosage will vary depending on the particular animal or human patient, age, body weight, symptom to be treated, desired therapeutic effect, administration route, term of treatment and the like, satisfactory effects will be obtained with the dosage of 0.001–500 mg/kg administered in 2 to 4 divided doses a day or as a sustained form.

As a solid composition of this invention for oral administration, tablets. troches, buccals, capsules, pills, powders, granules and the like are included. The solid composition containing one or more active substances is mixed with at least an inactive diluent, e.g. lactose, mannitol, glucose, hydrocypropyl cellulose, fine crystalline cellulose, starch, polyvinyl pyrolidone, magnesium aluminate metasilicate. The composition may contain additives other than the inactive diluent, for example, lubricants e.g., magnesium stearate, a disintegrator e.g. cellulose calcium gluconates, stabilizers e.g. a-, b- or x-cyclodextrins, etherated cyclodextrins (e.g. dimethyl-a-, dimethyl-b-, trimethyl-b-, or hydroxypropyl-b-cyclodextrins), branched cyclodextins (e.g. glucosyl- or maltosyl-cyclodextrins), formyl cyclodextrins, sulfur-containing cyclodextrins, misoprotols or phospholipids. Such cyclodextrins may increase the stability of the compounds by forming an inclusion compounds. The stability may be often increased by forming lyposome with phospholipids. Tablets and pills may be coated with an enteric or gastroenteric film e.g. white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed e.g. gelatin. The composition may be in the form of buccals, when an immediated effect is desired. For this purpose, base e.g. glycerine, lactose may be used.

Liquid compositions for oral administration include pharmaceutically acceptable emulsions, solutions, suspensions, syrups, elixirs and the like and contain a generally used inactive diluent e.g. purified water or ethyl alcohol. The composition may contain additives e.g. wetting agents, suspending agents, sweeteners, flavors, perfumes and preservatives.

The composition of the present invention may be sprays which may contain one or more active ingredients and which can be prepared according to a well known methods.

An injection of this invention for non-oral administration includes serile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils e.g. olive oil, alcohols, e.g. ethanol and polysorbates. The composition may contain other additives, e.g. preservatives, wetting agents, emulsifying agents, dispersing agents and the like. These are sterilized by filtration through, e.g. a bacteria- retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at least one active compound according to the invention with a suppository base e.g. cacao butter and optionally containing nonionic surfactant for improving absorption.

The compounds used in the medicament for improvement of excretion of nonprotein nitrogen into the intestines according to the present invention have an effect of improving excretion of nonprotein nitrogen in the blood into the intestine or as feces.

Accordingly, the compounds used in the present invention are useful for treatment (e.g. prevention, cure, relief and arrest or relief of development) of conditions wherein nonprotein nitrogen level in the blood is elevated and of uremia, irrespective of cause, e.g. disease, drug or food.

Further, the compounds of the present invention are also useful in case where the renal excretion of nonprotein nitrogen is damaged due to reduce in or loss of he renal function e.g. by renal failure.

A more complete understanding of the present invention can be obtained by reference to the following Formulation Examples and Test Examples which are provided herein for purpose of illustration only and are not intended to limit the scope of the invention.

Formulation Example 1

(Hard gelatin capsules)

| | |
|---|---|
| 13,14-dihydro-15-keto-16R,S-fluoro-PGE$_2$ | 50 mg |
| lactose | 200 mg |

The above ingredients were mixed and filled in hard gelatin capsules.

Formulation Example 2

(Powders for injection)

| | (Parts by weight) |
|---|---|
| 13,14-dihydro-15-keto-16,16-difluoro-PGE$_2$ | 1 |
| mannitol | 5 |
| distilled water | 0.4 |

The above ingredients were mixed, stirred, sterilized, filtered and lyophilized to give powders for injection.

Formulation Example 3

(Injectable solution)

| | (Parts by weight) |
|---|---|
| 13,14-dihydro-15-keto-16,16-dimethyl-PGE$_2$ | 0.2 |
| nonion surfactant | 2 |
| distilled water | 98 |

The above ingredients were mixed and sterilized to give and injectable solution.

Formulation Example 4

13,14-dihydro-15-keto-16,16-difluoro-20-ethyl-PGE$_2$ (50 mg) dissolved in methanol (10 ml) was mixed with mannitol (18.5g). The mixture was screened (with a sieve, the pore size of which being 30 mm in diameter), dried and screened again. The powders thus obtained were mixed with fine-grain silica gel (Aerosil*, 200 g) and filled in No.3 hard gelatin capsules (100) to give enteric capsules which contain 0.5 mg of 13,14-dihydro-15-keto-16,16-difluoro-20-ethyl-PGE$_2$ per capsule.
*Trade Mark Formulation Example 5

(Powders for oral administration)

| | (Parts by weight) |
|---|---|
| 13,14-dihyro-15-keto-16,16-difluoro-PGF$_{2\alpha}$ methyl ester | 5 |
| light anhydrous silicic acid | 5 |
| Abicel* | 20 |
| lactose | 70 |

*Trade Mark

The above ingredients were mixed to give powders for oral administration.

Formulation Example 6

(Soft gelatine capsules)

| | (Parts by weight) |
|---|---|
| 13,14-dihydro-15-keto-20-methyl-PGE$_2$ methyl ester | 1 |
| light anhydrous silicic acid | 899 |
| Panasate* | 20 |

*Trade Mark

The above ingredients were mixed and filled in soft gelatine capsules.

Formulation Example 7

(Enteric capsules)

16-desbutyl-13,14-dihydro-15-keto-16-(m-trifluoromethyl)phenoxy-PGF$_{2\alpha}$ methyl ester (50 mg) dissolved in methanol (10 ml) was mixed with mannitol (18.5 g). The mixture was screened (with a sieve, the pore size of which being 30 mm in diameter), dried for 90 minutes at 30° C. and screened again. The powders thus obtained were mixed with fine-grain silica gel (Aerosil*, 200 g) and filled in No. 3 hard gelatin capsules (100) to give enteric capsules which contain 0.5 mg of 13,14-dihydro-15-keto-16-desbutyl-16-m-trifluoromethylphenoxy-PGF$_{2\alpha}$ methyl ester per capsule.
*Trade Mark In the above formulation examples, the active ingredient can be replaced by any other compound within the compounds used in the invention.

Test Example 1

Thirty male Crj: Wistar rats (5 weeks old, obtained from Charles River) were quarantined and acclimatized for about 1 weeks. Then the animals were divided into groups with even mean weight and standard deviation.

All the animals were bred in individual stainless steel cages (190×380×180 mm) at a temperature of 24±1° C. and with a humidity of 55±5% with 12 hour light and dark cycle (illumination 8:00–20:00) supplying with fresh aseptic air. They were bred (with NMF, Oriental Yeast Industries, Ltd) and waterad ad libitum except the last day of medication, on which day they were fasted.

Test compound 13,14-dihydro-15-keto-16-R,S-fluoro-prostaglandian E$_2$ was dissolved in an aliquot of ethanol and the solution was evaporated in a test tube under nitrogen. The residue was combined with a predetermined amount of distilled water and sonicated to form a homogeneous test suspension.

Starting from day 1 to day 14, rats received (between 9:00 and 12:00) a daily dosage of 1 ml/1 kg of the test suspension through a disposable plastic sylinge (1 ml) equipped with an P.O. administration needle for rat based on the body weight measured just before the administration.

Design of the experiment was as follows:

| Group | Dose (mg/kg) | Number of rats |
|---|---|---|
| 1 | 0 | 5 |
| 2 | 0.1 | 5 |
| 3 | 2.0 | 5 |

All the animals were observed twice a day for any mortality and general conditions such as diarrhea except the last day, on which observation was made only once directly before the post mortem. The body weight and intake were measured every day at the predetermined time (between 9:00–10:00) before the medication. Urine collection (24 hr) was made between post-medication on day 13 and pre-medication on day 14 under fasting.

Directly after the last medication, rats were sacrificed by cervical dislocation and subjected to celiotomy. Intestine was ligated at pyloric part of stomach and upper cecal part. The whole small intestine was removed and intraintestinal content was collected, measured a volume and centrifuged at 1000 rpm and suppernatant was separated.

The urine, serum and supernatant were assayed for urea nitrogen (UN) and non-protein nitrogen (NPN) concentrations.

The results are summarized in the following Tables.

TABLE 1

| | | Body weight Weight (g) | | | | | | | | | | | | | |
|---|---|---|---|---|---|---|---|---|---|---|---|---|---|---|---|
| Dosage | Day | 1 | 2 | 3 | 4 | 5 | 6 | 7 | 8 | 9 | 10 | 11 | 12 | 13 | 14 |
| 0 | n | 5 | 5 | 5 | 5 | 5 | 5 | 5 | 5 | 5 | 5 | 5 | 5 | 5 | 5 |
| (Control) | mean | 277.7 | 280.0 | 291.9 | 296.2 | 307.3 | 312.3 | 320.4 | 329.7 | 334.9 | 340.8 | 346.4 | 350.1 | 356.0 | 318.0 |
| | S.D. | 4.1 | 7.9 | 6.7 | 7.6 | 10.8 | 10.9 | 12.5 | 10.8 | 11.7 | 14.1 | 15.6 | 15.2 | 16.5 | 13.5 |
| 0.1 | n | 5 | 5 | 5 | 5 | 5 | 5 | 5 | 5 | 5 | 5 | 5 | 5 | 5 | 5 |
| mg/kg | mean | 277.6 | 281.1 | 293.4 | 297.1 | 300.3 | 310.8 | 320.8 | 330.4 | 335.8 | 339.4 | 344.5 | 351.3 | 355.9 | 317.0 |
| | S.D. | 4.1 | 4.9 | 7.4 | 6.0 | 13.0 | 7.1 | 6.7 | 8.4 | 8.3 | 6.6 | 12.4 | 8.8 | 11.1 | 10.9 |
| 2.0 | n | 5 | 5 | 5 | 5 | 5 | 5 | 5 | 5 | 5 | 5 | 5 | 5 | 5 | 5 |
| mg/kg | mean | 277.6 | 274.7 | 283.0 | 286.7 | 296.9 | 300.7 | 309.6 | 319.9 | 322.7 | 327.8 | 330.8 | 334.1 | 345.9 | 304.9 |
| | S.D. | 3.0 | 5.0 | 3.7 | 4.5 | 4.8 | 4.8 | 4.6 | 8.2 | 6.5 | 8.7 | 6.8 | 7.7 | 7.9 | 6.6 |

TABLE 2

| | | Intake Intake (g) | | | | | | | | | | | |
|---|---|---|---|---|---|---|---|---|---|---|---|---|---|
| Dosage | Day | 1 | 2 | 3 | 4 | 5 | 6 | 7 | 8 | 9 | 10 | 11 | 12 |
| 0 | n | 5 | 5 | 5 | 5 | 5 | 5 | 5 | 5 | 5 | 5 | 5 | 5 |
| (Control) | mean | 27.8 | 28.5 | 29.8 | 28.2 | 28.2 | 30.0 | 29.1 | 29.1 | 30.1 | 29.3 | 29.9 | 29.7 |
| | S.D. | 3.1 | 2.6 | 2.6 | 1.9 | 3.0 | 2.1 | 2.4 | 2.4 | 2.7 | 3.1 | 2.1 | 2.9 |
| 0.1 mg/kg | n | 5 | 5 | 5 | 5 | 5 | 5 | 5 | 5 | 5 | 5 | 5 | 5 |
| | mean | 25.9 | 28.6 | 29.1 | 24.4 | 29.3 | 30.7 | 29.5 | 29.3 | 28.8 | 29.4 | 29.1 | 28.6 |
| | S.D. | 2.9 | 1.3 | 1.4 | 6.6 | 2.5 | 1.5 | 2.5 | 2.5 | 0.1 | 0.9 | 3.4 | 1.0 | 1.7 |
| 2.0 mg/kg | n | 5 | 5 | 5 | 5 | 5 | 5 | 5 | 5 | 5 | 5 | 5 | 5 |
| | mean | *19.3 | 24.8 | 26.1 | 25.2 | 26.3 | 28.1 | 29.0 | 27.8 | 28.7 | 29.1 | 28.0 | 30.9 |
| | S.D. | 1.4 | 1.6 | 2.6 | 2.3 | 2.3 | 2.3 | 2.7 | 1.0 | 1.0 | 2.7 | 2.7 | 2.5 |

*$0.05 > P > 0.01$
(DUNNET ANALYSIS)

TABLE 3

| | | Nitrogen (I.C.: Intraintestinal content) | | | | | |
|---|---|---|---|---|---|---|---|
| Dosage | | I.C. ml | Urine (3 hr) ml | I.C. mg | UN Urine mg | I.C. mg | NPN Urine mg |
| 0 | mean | 2.2 | 3.9 | 0.200 | 5.282 | 2.19 | 4.23 |
| (Control) | S.D. | 1.2 | 2.1 | 0.215 | 3.484 | 1.36 | 2.36 |
| 0.1 mg/kg | mean | 2.0 | 1.6 | 0.317 | *1.354 | 2.12 | *1.67 |
| | S.D. | 0.4 | 0.8 | 0.150 | 0.885 | 0.46 | 0.84 |

TABLE 3-continued

| | | Nitrogen (I.C.: Intraintestinal content) | | | | | |
|---|---|---|---|---|---|---|---|
| Dosage | | I.C. ml | Urine (3 hr) ml | I.C. mg | UN Urine mg | I.C. mg | NPN Urine mg |
| 2.0 mg/kg | mean | **4.8 | 1.8 | **0.637 | 1.882 | *4.40 | 1.97 |
| | S.D. | 1.8 | 1.0 | 0.165 | 1.219 | 1.13 | 1.03 |

**$0.1 > P$
*$0.05 > P > 0.01$
(DUNNET analysis)

From the above results, it can be easily understood that excretion of urea nitrogen and nonprotein nitrogen into the intestine was dose-dependently increased in the medicated group. Almost no influence was observed in the medicated group in respect to body weight and water intake.

TEST EXAMPLE 2

Male Wistar rats (8 weeks old) were anesthetized with pentobarbital (40 mg/kg) and cortices of their left kidneys were partly removed. After 3 to 7 days, their whole right kidneys were removed. The overall excision of kidneys were 1 plus three fourths to 1 plus four fifths. As the test compound, 13,14-dihydro-15-keto-16-R,S-fluoro-prostaglandin $E_2$ methyl ester was suspended in distilled water and administered orally to the surgically injured animals (3 per group) at a dose of 2 mg/kg/ml on continuous 14 days starting from the day after 14 days the operation. The dose was increased to 3 mg/kg on and after day 10 of administration because animals came to have not diarrhea about that day. The control group received the same volume of distilled water. One week after the start of medication, blood samples were taken from tail vein of each animal and serum was assayed for blood urea nitrogen (UN) and creatinine (CRE) concentrations.

In addition two weeks after the start of medication, the total blood was taken from ventral aorta of each animal and serum was assayed for urea nitrogen (UN) and creatinie (CRE) concentrations. After 2 hours of the last medication, feces were collected and extracted with a predetermined amount of water. The extract was centrifuged and the supernatant was assayed for electrolytes. Weight and water intake of the rats were measured at almost daily.

The results are summarized in the following Tables.

TABLE 4

| | Weight (g) | | | |
| | Control group | | Test group | |
| Days of medication | mean | SD | mean | SD |
|---|---|---|---|---|
| 0 | 332.2 | 31.3 | 341.7 | 23.9 |
| 1 | 345.9 | 35.3 | 321.8 | 24.3 |
| 2 | 324.0 | 23.0 | 311.8 | 15.7 |
| 3 | 345.4 | 25.7 | 313.8 | 10.8 |
| 4 | 339.4 | 22.5 | 319.3 | 10.3 |
| 5 | 344.9 | 25.1 | 336.7 | 12.8 |
| 7 | 352.7 | 31.0 | 351.6 | 15.5 |
| 8 | 348.9 | 25.7 | 341.9 | 17.4 |
| 9 | 335.6 | 26.0 | 341.0 | 15.6 |
| 10 | 360.6 | 32.8 | 348.6 | 23.5 |
| 11 | 360.6 | 21.1 | 359.6 | 20.3 |
| 12 | 355.2 | 28.2 | 356.7 | 17.1 |
| 13 | 257.9 | 27.2 | 359.5 | 20.2 |
| 14 | 337.7 | 8.6 | 364.8 | 15.0 |

TABLE 5

| | Water intake (ml/day) | | | |
| | Control group | | Test group | |
| Days of medication | mean | SD | mean | SD |
|---|---|---|---|---|
| | 77.6 | 12.4 | 44.2 | 7.1 |
| 2 | 72.1 | 10.2 | 51.4 | 4.5 |
| 3 | | | 48.3 | 13.7 |
| 4 | 69.0 | 10.2 | 66.3 | 16.3 |
| 5 | 74.6 | 9.5 | 99.8 | 18.3 |
| 8 | 70.6 | 5.1 | 99.8 | 18.3 |
| 9 | 73.4 | 7.0 | 95.9 | 16.1 |
| 10 | 75.4 | 5.0 | | |
| 11 | 71.3 | 7.1 | 88.8 | 5.2 |
| 12 | 73.8 | 3.2 | 81.5 | 9.8 |
| 13 | 72.1 | 4.3 | 89.5 | 5.9 |

TABLE 6

| | Serum | | |
| Group | | BUN (mg/dl) | CRE (mg/dl) |
|---|---|---|---|
| untreated | mean | 25.1 | 0.4 |
| | ±SD | ±2.6 | ±0 |
| 2 weeks after | mean | 92.7 | 1.35 |
| operation | ±SD | ±23.8 | ±0.44 |
| medicated | mean | 91.8 | 1.57 |
| control | ±SD | ±19.1 | ±0.4 |
| 1 week | mean | 62.9** | 1.03** |
| medicated | ±SD | ±5.2 | ±0.15 |
| medicated | mean | 102.1 | 1.57 |
| control | ±SD | ±32.7 | ±0.40 |
| 2 weeks | mean | 75.7** | 1.00** |
| medicated | ±SD | ±14.4 | ±0.15 |

*P < 0.05
**P < 0.1

TABLE 7

| | Serum | |
| | control mean ± S.D. | 2 mg/kg mean ± S.D. |
|---|---|---|
| UN (mg/dl) | 102.1 ± 32.7 | 75.7 ± 14.4 |
| CRE (mg/dl) | 1.6 ± 0.4 | 1.0 ± 0.2 |

TABLE 8

| | Feces (2 weeks medication) | | |
| group | | UN mg | CRE mg |
|---|---|---|---|
| control | mean | 3.05 | 0.058 |
| test | mean | 12.01 | 0.25 |
| | ±SD | ±5.48 | ±0.06 |

From the above result, it can be clearly seen that, after two weeks of renal injury, urea nitrogen and creatine concentrations in the blood was increased in the injured group by about 3.7 and 3.4 times, respectively as compared with the intact group and that, after two weeks of the onset of medication, urea nitrogen and creatinine concentrations were decreased in the medicated group as compared with the control group wherein concentrations were at high levels and further, after 2 hours of medication, urea nitrogen and creatinine in feces of the medicated group were four times larger than in feces of the control group.

Test Example 3

Male Wistar rats (8 weeks old) were anesthetized by pentobarbital (40 mg/kg, i.p.) and cortex of the left kidney was partly excised. After 3 to 7 days, the right kidney was totally excised. The over all excision of the kidney was 1 plus three fourths to 1 plus four fifths. As the test compound, 13,14-dihydro-15-keto-16R,S-fluoro-PGE$_2$ was suspended in distilled water, homogenized and then orally administered, at a rate of 3 mg/kg/ml, continuously for a period of two weeks starting from the day after two weeks of the excision of the kidneys (three animal per group). The control group orally received the same volume of distilled water.

Feces were collected one week after the administration and the intestinal contents were collected two weeks after the administration. These were assayed for excretion of urea nitrogen (UN) and creatinine (CRE).

In addition, blood samples were collected from a jugular vein without anesthesia one week after the administration and assayed for urea nitrogen and creatinine. Also, body weight and water intake were measured from a day before the experiment to the last day of the experiment. The results are shown in the following Tables, in which * denotes P<0.1,  P<0.05 and * P<0.01.

TABLE 9

| | Body Weight and Water Intake | | | | | | | |
| | Body weight | | | | Water Intake | | | |
| | Control | | Medicated | | Control | | Medicated | |
| Day | Mean | S.D. | Mean | S.D. | Mean | S.D. | Mean | S.D. |
|---|---|---|---|---|---|---|---|---|
| −2 | 316 | ±20 | 322 | ±12 | | | | |
| −1 | 317 | ±26 | 330 | ±15 | 84.7 | ±20.4 | 101.9 | ±14.0 |
| 0 | 307 | ±42 | 324 | ±10 | | | | |

TABLE 9-continued

| | Body Weight and Water Intake | | | | | | | |
|---|---|---|---|---|---|---|---|---|
| | Body weight | | | | Water Intake | | | |
| | Control | | Medicated | | Control | | Medicated | |
| Day | Mean | S.D. | Mean | S.D. | Mean | S.D. | Mean | S.D. |
| 1 | 316 | ±35 | 325 | ±14 | 98.6 | ±19.1 | 53.3 | ±12.2 |
| 2 | 315 | ±31 | 321 | ±21 | 98.6 | ±19.1 | 53.3 | ±12.2 |
| 3 | 317 | ±27 | 320 | ±31 | 87.8 | ±12.1 | 62.7 | ±21.7 |
| 4 | 320 | ±24 | 328 | ±31 | 100.0 | | 76.2 | ±26.8 |
| 5 | 322 | ±27 | 327 | ±35 | 96.0 | ±14.8 | 68.6 | ±19.7 |
| 6 | 327 | ±28 | 333 | ±33 | 96.0 | ±14.8 | 68.6 | ±17.7 |
| 7 | 331 | ±25 | 347 | ±36 | 94.7 | ±18.8 | 78.3 | ±13.9 |
| 8 | 321 | ±21 | 334 | ±30 | 94.7 | ±18.8 | 78.3 | ±13.9 |
| 9 | 315 | ±30 | 342 | ±25 | | | | |
| 10 | 316 | ±35 | 341 | ±26 | 82.3 | ±10.0 | 105.8 | ±2.8 |
| 11 | 317 | ±38 | 335 | ±30 | 82.3 | ±10.7 | 105.8 | ±2.8 |
| 12 | 324 | ±27 | 347 | ±31 | 96.8 | ±13.4 | 94.4 | ±17.7 |
| 13 | 320 | ±25 | 356 | ±31 | | | | |
| 14 | 333 | ±31 | 349 | ±34 | 96.8 | ±13.4 | 94.4 | ±17.7 |

TABLE 10

| Assay of Serum | | | |
|---|---|---|---|
| | | UN mg/dl | CRE mg/dl |
| Control | Mean | 141.2 | 1.7 |
| | S.D. | ±33.0 | ±0.4 |
| Medicated | Mean | 97.3* | 1.3 |
| (3.0 mg/kg) | S.D. | ±24.8 | ±0.3 |

From the above results, it can be easily understood that urea nitrogen and creatinine in the blood were significantly decreased in the medicated group.

Almost no influence was observed in the medicated group in respect to body weight and water intake.

TABLE 11

| Assay of Feces | | | | |
|---|---|---|---|---|
| Day | | | UN mg | CRE mg |
| 2 | Control | Mean | 1.07 | 0.02 |
| | | S.D. | ±0.63 | ±0.01 |
| | Medicated | Mean | 3.54** | 0.12** |
| | | S.D. | ±1.10 | ±0.06 |
| 7 | Control | Mean | 0.40 | 0.14 |
| | | S.D. | ±0.04 | ±0.05 |
| | Medicated | Mean | 1.42*** | 0.29 |
| | | S.D. | ±0.12 | ±0.09 |

From the above results, it can be clearly seen that urea nitrogen and creatinine were significantly excreted in the feces or the intestinal contents.

Test Examples 4

The procedure of Test Example 3 was repeated except that 13,14-dihydro-15-keto-16,16-difluoro-PGE$_2$ (1.0 mg/kg) was used as the test compound. Assays were performed with the feces at day 5 and the intestinal contents at day 14. The results are shown in the following Tables.

TABLE 12

| Day | | | UN mg | CRE mg |
|---|---|---|---|---|
| 5 | Control | Mean | 3.42 | 0.051 |
| | | S.D. | ±1.86 | ±0.025 |
| | Medicated | Mean | 3.57 | 0.235** |
| | | S.D. | ±0.99 | ±0.124 |

TABLE 13

| Assay of Intestinal Contents | | | | |
|---|---|---|---|---|
| Day | | | UN mg | CRE mg |
| 14 | Control | Mean | 0.07 | 0.17 |
| | | S.D. | ±0.07 | ±0.06 |
| | Medicated | Mean | 0.64** | 0.21 |
| | | S.D. | ±0.41 | ±0.06 |

What we claim is:

1. A method for lowering the concentration of nonprotein nitrogen in circulating blood of a patient which comprises administering, to a patient in need of such lowering, a prostanoic acid derivative of formula (I) in an amount sufficient to cause the excretion of nonprotein nitrogen from the circulating blood of the patient into the intestine of the patient:

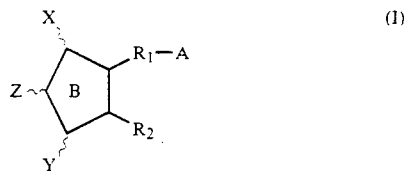

in which ring B is saturated or contains at least one double bond, each of X and Y is independently selected from the group consisting of a hydrogen atom, hydroxy, a halogen atom, lower alkyl, hydroxy(lower)alkyl and oxo, at least one of X and Y not being hydrogen, Z is hydrogen or halogen atom, A is —CH$_2$OH, —COCH$_2$OH, or —COOH or a pharmaceutically acceptable salt, ester or amide of —COOH, R$_1$ is a bivalent saturated or unsaturated, lower or medium length aliphatic hydrocarbon residue which is unsubstituted or substituted by halo, oxo or aryl, and R$_2$ is a saturated or unsaturated, lower or medium length aliphatic hydrocarbon residue which is unsubstituted or substituted with oxo, hydroxy, halo, lower alkoxy, lower alkanoyloxy, cyclo(lower) alkyl, aryl or aryloxy, with the proviso that in R$_2$ the third carbon atom counted from ring C is substituted by oxo in an amount effective in improving excretion of nonprotein nitrogen into the intestines.

2. The method according to claim 1, for reducing nonprotein nitrogen concentration in the blood.

3. The method according to claim 1, wherein the nonprotein nitrogen is urea nitrogen or creatinine.

4. The method according to claim 1, for compensating reduced renal function.

5. The method according to claim 1, for treating renal insufficiency.

6. The method according to claim 1, wherein the prostanoic acid derivative is a prostaglandin which has one or two halogen atoms at position 16.

7. The method according to claim 1, wherein the prostanoic acid derivative is a prostaglandin which has an oxo group at position 15.

8. The method according to claim 1, wherein the prostanoic acid derivative is a prostaglandin which has a saturated bond between positions 13 and 14.

9. The method according to claim 1, wherein the prostanoic acid is a prostaglandin derivative.

10. The method according to claim 1, wherein the prostanoic acid derivative is a 15-keto-16-mono- or -di-fluoroprostaglandin compound.

11. The method according to claim 1 wherein in $R_2$, the fourth carbon atom counted from ring B is substituted by halo.

12. The method according to claim 11, wherein said fourth carbon atom is substituted by one halogen atom.

13. The method according to claim 11, wherein said fourth carbon atom is substituted by two halogen atoms.

14. The method according to claim 1, wherein in $R_2$ the bond between the first and second carbon atoms, counted from ring C is a saturated bond.

15. The method according to claim 1, wherein $R_1$ and $R_2$ each is a straight or branched-chain hydrocarbyl group having 1 to 14 carbon atoms.

16. The method according to claim 1, wherein $R_1$ is a straight or branched-chain hydrocarbyl group having 2 to 8 carbon atoms and $R_2$ is a straight or branched-chain hydrocarbyl group having 6 to 12 carbon atoms.

* * * * *